United States Patent
Wu et al.

(10) Patent No.: US 12,372,231 B2
(45) Date of Patent: Jul. 29, 2025

(54) DEVICE AND METHOD FOR PRODUCING HIGH-PRESSURE OR SUPER HIGH-PRESSURE STEAM AS BYPRODUCT FROM MALEIC ANHYDRIDE PRODUCING DEVICE

(71) Applicant: CHANGZHOU RUIHUA CHEMICAL ENGINEERING TECHNOLOGY CO., LTD., Changzhou (CN)

(72) Inventors: Feike Wu, Changzhou (CN); Wenming Zhang, Changzhou (CN); Hu Chen, Changzhou (CN); Ruyi Zhu, Changzhou (CN); Hongjiang Dong, Changzhou (CN); Yifei Zhou, Changzhou (CN); Xia Chen, Changzhou (CN); Zhigang Xu, Changzhou (CN)

(73) Assignee: CHANGZHOU RUIHUA CHEMICAL ENGINEERING TECHNOLOGY CO., LTD., Changzhou (CN)

( * ) Notice: Subject to any disclaimer, the term of this patent is extended or adjusted under 35 U.S.C. 154(b) by 0 days.

(21) Appl. No.: 18/809,731

(22) Filed: Aug. 20, 2024

(65) Prior Publication Data

US 2024/0410567 A1 Dec. 12, 2024

Related U.S. Application Data

(63) Continuation of application No. PCT/CN2024/071196, filed on Jan. 8, 2024.

(30) Foreign Application Priority Data

Jan. 12, 2023 (CN) .......................... 202310041536.7

(51) Int. Cl.
*F22B 1/06* (2006.01)
*B01J 19/00* (2006.01)
*C07D 307/60* (2006.01)

(52) U.S. Cl.
CPC ............. *F22B 1/06* (2013.01); *B01J 19/0013* (2013.01); *C07D 307/60* (2013.01); *B01J 2219/00054* (2013.01); *B01J 2219/00103* (2013.01)

(58) Field of Classification Search
CPC ....................................................... F22B 1/06
See application file for complete search history.

(56) References Cited

U.S. PATENT DOCUMENTS

| | | | |
|---|---|---|---|
| 3,171,791 A | 3/1965 | Wootton | |
| 4,169,098 A * | 9/1979 | Hellmer | C07C 51/265 |
| | | | 549/248 |
| 5,869,011 A | 2/1999 | Lee | |

FOREIGN PATENT DOCUMENTS

| | | | | |
|---|---|---|---|---|
| CN | 1733746 A | | 2/2006 | |
| CN | 102635845 A | | 8/2012 | |
| CN | 107100684 A | | 8/2017 | |
| CN | 108727313 A | | 11/2018 | |
| CN | 110142007 A | | 8/2019 | |
| CN | 213983493 | * | 8/2021 | ............... F22B 1/06 |
| CN | 213983493 U | | 8/2021 | |
| CN | 217383919 U | | 9/2022 | |

OTHER PUBLICATIONS

First Search Report issued in counterpart Chinese Patent Application No. 202310041536.7, dated Sep. 12, 2023.
Notification to Grant Patent Right for Invention issued in counterpart Chinese Patent Application No. 202310041536.7, dated Sep. 19, 2023.

* cited by examiner

*Primary Examiner* — Nizal S Chandrakumar
(74) *Attorney, Agent, or Firm* — Westbridge IP LLC (57) ABSTRACT

Disclosed are a device and a method for producing high-pressure or super high-pressure steam as a byproduct from a maleic anhydride producing device. The device includes a super high-pressure steam drum, a molten salt pump, an oxidation reactor, a regulating valve, molten salt coolers, a switching cooler and a gas cooler. The molten salt pump, the oxidation reactor, the regulating valve and the molten salt coolers are connected. A boiler water buffer device and a boiler water booster pump are arranged between the switching cooler and the gas cooler. The unique design of the boiler water intermediate pressure boosting and the gas cooler in the disclosure makes the gas cooler and the switching cooler very easy to manufacture. Heat can be effectively recovered from process gas to produce high-pressure or super high-pressure steam while accumulation of dust in the process gas is avoided and tar adhesion is easy to clean.

7 Claims, 3 Drawing Sheets

DEVICE AND METHOD FOR PRODUCING HIGH-PRESSURE OR SUPER HIGH-PRESSURE STEAM AS BYPRODUCT FROM MALEIC ANHYDRIDE PRODUCING DEVICE

CROSS-REFERENCE TO RELATED APPLICATIONS

This application is a continuation of International Application No. PCT/CN2024/071196, filed on Jan. 8, 2024, which claims priority to Chinese Patent Application No. 202310041536.7, filed on Jan. 12, 2023. All of the aforementioned applications are incorporated herein by reference in their entireties.

TECHNICAL FIELD

The disclosure relates to the technical field of maleic anhydride production, and in particular relates to a device and method for producing high-pressure or super high-pressure steam as a byproduct from a maleic anhydride producing device.

BACKGROUND

Cis-butenedioic anhydride, also known as maleic anhydride, is an important organic chemical raw material and the third largest organic acid anhydride in the world after phthalic anhydride and acetic anhydride, and is widely used in petrochemicals, food processing, pharmaceuticals, building materials and other industries. In recent years, due to rapid development of degradable plastics, the demand for 1,4-butanediol (BDO), an important raw material for degradable plastics, has increased rapidly in the market, which has also driven the production demand for upstream maleic anhydride.

At present, based on a raw material route, the methods for producing maleic anhydride include a benzene oxidation method and an n-butane oxidation method. A traditional process is mainly based on benzene oxidation, but due to the carcinogenicity of benzene and high cost of raw materials, the current newly built devices all use n-butane as the raw material. A typical device for producing maleic anhydride by oxidation of n-butane basically includes a reaction unit and a post-treatment unit. N-butane undergoes catalytic oxidation reaction with air to produce maleic anhydride. The mixing ratio of the n-butane to the air is typically 1.5-2.1 mol %, and the reaction uses a V/P system catalyst with a reaction temperature of 400-430° C. A hot-spot temperature of a reactor is typically 420-480° C. The reactor is a tubular fixed-bed reactor, and reaction heat is conducted out by circulating molten salt outside a reaction tube to control the temperature of the oxidation reaction. The heated molten salt outside the reaction tube enters a molten salt cooler, and the hot molten salt vaporizes water in the molten salt cooler to produce saturated steam. Finally, the reaction heat of the oxidation reactor is conducted out in the form of steam. The temperature of gas at an outlet of the reactor is about 390-435° C. After being cooled to 130-160° C. by a reaction gas cooler (gas cooler) and a switching cooler (switching cooler), the reaction gas enters the post-treatment unit of maleic anhydride. In the post-treatment unit, maleic anhydride in the reaction gas is absorbed and enters a desorption column for desorption to obtain crude maleic anhydride, and the crude maleic anhydride is refined to obtain a maleic anhydride product.

In the latest book "Light Hydrocarbon Processing Technology and Engineering" edited by Sun Lili (Sun Lili, China Petrochemical Press, 2020), the main process and engineering situation of an n-butane oxidation maleic anhydride production technology are systematically introduced, and typical process flows of Huntsman, ALMA and Conser are introduced, but a method and details for producing byproduct steam are not detailed. However, typical operating parameters for producing byproduct steam in a current n-butane method maleic anhydride producing device are introduced on pages 601-604: the operating pressure is 4.1-4.3 MPag, and the byproduct steam volume is 7-8 t/t maleic anhydride (excluding self-used~3 t/t maleic anhydride).

Due to a relatively small production scale of maleic anhydride (mainly 50,000 tons/year production device), the utilization of byproduct steam from maleic anhydride has not been highly valued all along. But with rapid development of degradable plastics, the demand for upstream 1,4-butanediol and maleic anhydride has increased rapidly. The typical scale of a maleic anhydride producing device currently in operation has reached 200,000 tons/year, with the maximum single unit scale reaching 600,000 tons/year, and the production scale of a single reactor under construction has also reached 67,000 tons/year. Taking the smaller typical scale of 200,000 ton/year of an n-butane method maleic anhydride producing device as an example, the hourly byproduct steam output of a reaction unit will reach 2-2.2 million tons/year, which is 10-11 times higher than the production scale of the main product maleic anhydride. The economic efficiency of the byproduct steam is even equal to or higher than that of the main product maleic anhydride in the market at certain times. Therefore, maximizing utilization of the reaction heat of a maleic anhydride producing device and maximizing the production of higher grade and more economically beneficial byproduct steam is of great significance for improving the economic efficiency of the maleic anhydride producing device.

Unfortunately, the n-butane method maleic anhydride producing devices currently put into operation mainly produce 4.0-5.5 MPag steam as a byproduct, which is insufficient and inefficient for utilization of the reaction heat of n-butane oxidation. The main reason is that the typical reaction temperature of n-butane oxidation reaction is 400-430° C., the temperature of hot molten salt entering a molten salt cooler is also maintained at 400-430° C., while the saturated temperature of 4.0-5.5 MPag steam is 252-265° C. The heat transfer temperature difference on a cold and hot side is as high as 135-178° C., which is extremely unreasonable in cascade utilization of energy consumption. Although Huizhou Yuxin Chemical Co., Ltd. has recently succeeded in attempting to produce higher-pressure steam (~8 MPag) as a byproduct on a maleic anhydride producing device newly put into operation, there is still great room for improvement from the perspective of reasonable setting of the heat transfer temperature difference and effective utilization of reaction heat.

In engineering, it is reasonable to control an operating temperature difference at 10-20° C. for a liquid/evaporation heat transfer system based on a balance among initial investment, operability and operating cost. Therefore, in a case that the operating temperature of molten salt on a hot side is 400-430° C., the heated side stream may be heated to a maximum of greater than or equal to 380° C. If the heated side stream is water, an n-butane oxidation unit may produce a maximum of 22 MPag subcritical or supercritical steam. Typically, steam with a pressure of 6-12 MPa is referred to as high-pressure steam, steam with a pressure of 12-16 MPa is referred to as super high-pressure steam, and steam with a pressure greater than 17 MPa is referred to as subcritical or supercritical steam.

Although from the perspective of the heat transfer temperature difference, an n-butane method maleic anhydride producing device may produce steam up to 22 MPag, the n-butane method maleic anhydride producing device has the main purpose of producing maleic anhydride and the secondary purpose of producing steam. Therefore, in addition to considering the heat transfer temperature difference, the operability of the device should also be considered to ensure stable and reliable operation of the n-butane method maleic anhydride producing device. Accordingly, generally speaking, it is feasible and economical to set the operating heat transfer temperature difference greater (30-40° C.) from the perspective of a process. In addition, considering the initial high activity and low operating temperature of a catalyst (~390° C.), it is possible for an n-butane method maleic anhydride producing reaction unit to produce byproduct super high-pressure steam of ~350° C. and 16.5 Mpa, while ensuring normal production of an n-butane oxidation maleic anhydride producing device. Nevertheless, considering that higher pressure and temperature in steam production have higher requirements for boiler water quality, according to the requirements of GB12145-2016, it is more appropriate to determine the maximum steam pressure of the n-butane method maleic anhydride producing device at 15.6 MPag.

The above discussion demonstrates the feasibility of producing byproduct super high-pressure steam from the n-butane method maleic anhydride producing device. However, it is not simple to implement the operation. To illustrate this problem, it is necessary to further illustrate a process and a traditional method of oxidation reaction outlet gas in an n-butane method.

At present, oxidation reactions of n-butane method maleic anhydride producing devices all use a V/P system catalyst. Such a catalyst can catalyze n-butane to highly selectively generate maleic anhydride, but has a significant disadvantage of low strength. Dust may be blown out during normal production, and a small amount of high freezing point tar may accumulate at an outlet of a reactor. Therefore, to avoid accumulation of the dust and tar in the device, in a traditional solution, process gas after the reaction is cooled in two stages, namely a first-stage cooler (also referred to as a gas cooler) and a second-stage cooler (also referred to as a switching cooler). The process gas undergoes heat exchange in the tube pass of the cooler. The first-stage cooler is designed to reduce a dead zone and prevent catalyst dust from accumulating in the device. The second-stage cooler is to be regularly switched and cleaned (due to precipitation and adhesion of high freezing point tar on the inner wall of a heat exchange tube in a cooling process, resulting in a rapid deterioration of the heat transfer effect). Therefore, for the convenience of cleaning, the process gas is also designed in the tube pass. The shell passes of the first-stage cooler and the second-stage cooler are used for preheating boiler feedwater and generating 4-5 MPa steam. Such a design is reasonable and has been validated in existing operating devices.

It is difficult to directly produce high-pressure or super high-pressure steam by traditional methods by simply increasing the operating pressure and design pressure. Although Huizhou Yuxin has achieved production of byproduct steam of ~8 MPag by a traditional process in a newly built n-butane method maleic anhydride producing device, there are still some problems to be improved. In addition, a traditional method is no longer suitable in situations where the production scale of a single device or the pressure of byproduct steam is to be improved.

The main problems are as follows.

The gas cooler and the switching cooler use a fixed tube sheet structure, and the process gas flows through the tube pass to prevent blockage or facilitate cleaning, but a new problem is brought about. Due to the fixed tube sheet structure of the gas cooler and the switching cooler, large temperature difference between the tube passes and the shell passes of the gas cooler and the switching cooler, as well as changes in the operating condition, expansion joints are to be arranged on device shell sides to absorb the difference in expansion caused by temperature difference between the tube passes and the shell passes, and avoid damage to the device caused by excessive stress. Such a solution is feasible for traditional production of byproduct medium-pressure steam of 4-5.5 MPag. But if higher pressure steam is to be produced, the operation and design pressure of the shell pass may increase and cause difficulties in designing and manufacturing the shell pass expansion joints and implementing a project. Even if the project is reluctantly achieved, the investment and risk of the device may significantly increase.

Due to increase in the pressure of byproduct steam, the temperature difference between the tube pass and the shell pass of the molten salt cooler is much smaller than that of byproduct steam of 4-5 MPag. Therefore, the required device heat exchange area may also be much larger, which means that both the diameter and length of the molten salt cooler are to be increased. For high-pressure devices, an increase in the device diameter may lead to a rapid increase in investment, and the device diameter cannot be infinitely increased. Blindly increasing the device diameter may not only lead to a significant increase in device investment, but also create difficulties in manufacturing and impracticability.

To solve the above problems, the disclosure provides a device and method for producing high-pressure or super high-pressure steam as a byproduct from a maleic anhydride producing device, to solve the problems of difficulty and high cost in producing high-pressure or super high-pressure steam by existing devices.

SUMMARY

The objective of the disclosure is to provide a device and method for producing high-pressure or super high-pressure steam as a byproduct from a maleic anhydride producing device, to reduce the difficulty and cost in producing high-pressure or super high-pressure steam.

To achieve the above objective, the disclosure provides the following solutions.

A device for producing high-pressure or super high-pressure steam as a byproduct from a maleic anhydride producing device includes a super high-pressure steam drum as well as a first path and a second path respectively connected in parallel to the super high-pressure steam drum, wherein the first path includes a molten salt pump, an oxidation reactor, a regulating valve and molten salt coolers sequentially connected; the second path includes a switching cooler and a gas cooler sequentially connected; and a boiler water buffer device and a boiler water booster pump are sequentially arranged and connected between the switching cooler and the gas cooler.

Preferably, the boiler water buffer device is a boiler water buffer tank or a high-pressure deaerator.

Preferably, the gas cooler includes a first shell, a first boiler water inlet and a first boiler water outlet arranged at the top of the first shell, a process gas outlet arranged at the bottom of the first shell, a process gas inlet arranged at the side of the first shell, and a plurality of U-tube bundles and rod baffles arranged inside the first shell; and a distribution ring is arranged at the process gas inlet.

Preferably, more than one molten salt coolers are arranged and sequentially connected in series to the super high-pressure steam drum respectively.

Preferably, the molten salt regulating valve is connected to the at least two molten salt coolers through cold salt channels and hot salt channels; the molten salt coolers are connected to the oxidation reactor through a reactor salt channel; and a second boiler water inlet and a steam water mixture outlet are arranged on each of the molten salt coolers.

Preferably, a support beam is arranged between the molten salt coolers and the oxidation reactor.

A device for producing high-pressure or super high-pressure steam as a byproduct from a maleic anhydride producing device, wherein the installation height of the super high-pressure steam drum is 10-25 m higher than that of the molten salt coolers.

A method for producing high-pressure or super high-pressure steam as a byproduct from a maleic anhydride producing device, including the following steps:
  a) heat recovery from low-temperature process gas: boiler feedwater passes through a shell pass of the switching cooler and is heated by low-temperature reacted process gas in a tube pass;
  b) boiler water pressure boosting: the pressure of boiler water flowing out of the switching cooler is boosted by using the boiler water booster pump high enough to enter the super high-pressure steam drum;
  c) heat recovery from high-temperature process gas: the boosted boiler water is conveyed into the gas cooler and heated by high-temperature process gas at the outlet of the oxidation reactor; and
  d) generation of high-pressure or super high-pressure steam: the heated boiler water enters the super high-pressure steam drum and then enters the molten salt coolers, and the generated high-pressure or super high-pressure steam is separated from a liquid phase in the drum and flows out.

Preferably, in step a), the temperature of boiler feedwater entering the switching cooler is less than or equal to 125° C.; the pressure of the boiler feedwater entering the switching cooler is less than or equal to 4 MPa; and the temperature of process gas entering the switching cooler is 240-300° C.

Preferably, in step b), boiler water enters the boiler water buffer tank or the high-pressure deaerator before being boosted by the pump; the operating pressure of the boiler water entering the boiler water buffer tank is less than or equal to 3 MPag; and the operating pressure of the boiler water entering the high-pressure deaerator is 0.3-2.0 MPag.

The disclosure achieves the following technical effects compared to the prior art.

Firstly, the unique design of the boiler water intermediate pressure boosting and the gas cooler in the disclosure cleverly avoids device design challenges, and makes the gas cooler and the switching cooler very easy to manufacture. Heat can be effectively recovered from process gas to produce high-pressure or super high-pressure steam while accumulation of dust in the process gas is avoided and tar adhesion is easy to clean.

Secondly, a plurality of molten salt coolers are arranged in one oxidation reactor in the disclosure to divide the total reaction heat into multiple parts and reduce the heat transfer load of a single molten salt cooler, so that the heat transfer area of the molten salt coolers can meet the needs of producing high-pressure or super high-pressure steam, and the difficulty and risk in manufacturing the molten salt coolers are greatly reduced.

Lastly, the production method of the disclosure can significantly increase the pressure of byproduct steam of a maleic anhydride producing device up to 15.6 MPag, significantly reduce energy consumption of the device, and have high economic efficiency.

BRIEF DESCRIPTION OF THE DRAWINGS

To more clearly illustrate the technical solutions in the disclosure or the prior art, the drawings to be used in the examples will be briefly introduced below. Apparently, the drawings in the following description are only some examples of the disclosure. For those of ordinary skill in the art, other drawings may also be obtained from these drawings without creative work.

DETAILED DESCRIPTION OF THE EMBODIMENTS

The technical solutions in the examples of the disclosure will be clearly and completely described below with reference to the accompanying drawings in the examples of the disclosure. Apparently, the described examples are only a part, but not all, of the examples of the disclosure. Based on the examples of the disclosure, all other examples obtained by those of ordinary skill in the art without creative efforts shall fall within the protection scope of the disclosure.

The objective of the disclosure is to provide a device and method for producing high-pressure or super high-pressure steam as a byproduct from a maleic anhydride producing device, to reduce the difficulty and cost in producing high-pressure or super high-pressure steam.

To make the above objective, features and advantages of the disclosure clearer and easier to understand, the disclosure will be further described in detail below with reference to the accompanying drawings and examples.

Figure 1:
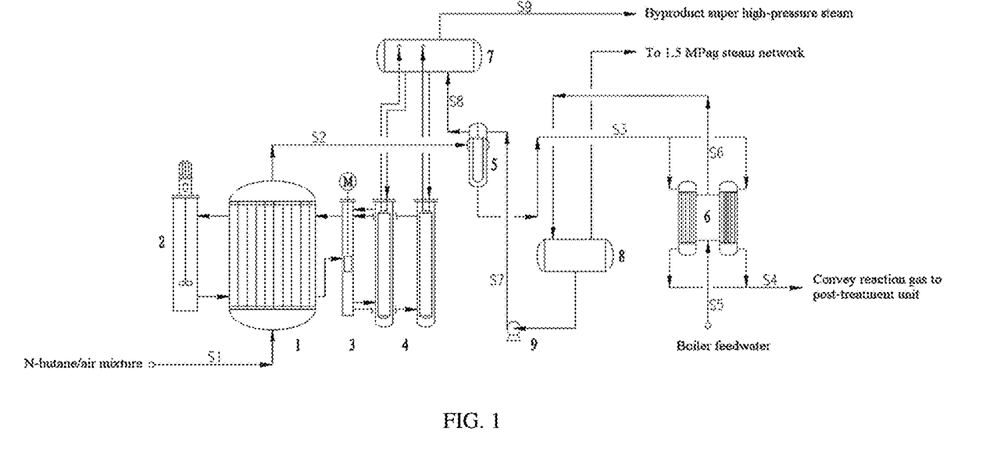
FIG. 1 is a flowchart of an oxidation unit of an n-butane method maleic anhydride producing device of the disclosure.

Referring to FIG. 1, a device for producing high-pressure or super high-pressure steam as a byproduct from a maleic anhydride producing device, includes a super high-pressure steam drum 7 as well as a first path and a second path respectively connected in parallel to the super high-pressure steam drum 7. The first path includes a molten salt pump 2, an oxidation reactor 1, a regulating valve and molten salt coolers 4 sequentially connected. The second path includes a switching cooler 6 and a gas cooler 5 sequentially connected. A boiler water buffer device and a boiler water booster pump 9 are sequentially arranged and connected between the switching cooler 6 and the gas cooler 5.

Further, the boiler water buffer device is a boiler water buffer tank 8 or a high-pressure deaerator.

Figure 3:
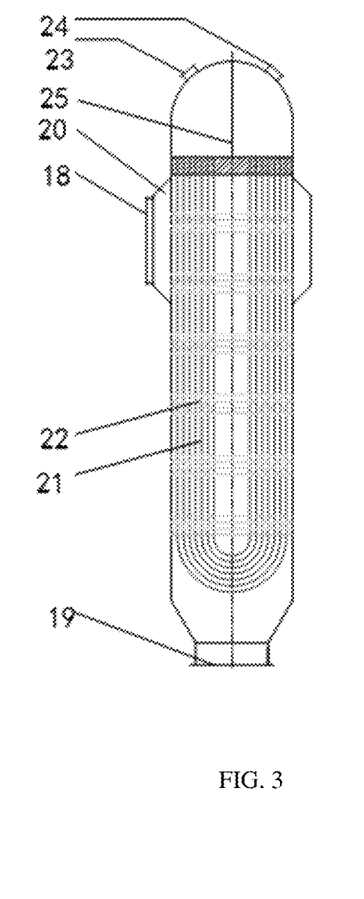
FIG. 3 is a schematic structural diagram of a gas cooler of the disclosure.

Referring to FIG. 3, the gas cooler 5 includes a first shell, a first boiler water inlet and a first boiler water outlet arranged at the top of the first shell, a process gas outlet arranged at the bottom of the first shell, a process gas inlet 18 arranged at the side of the first shell, and a plurality of U-tube bundles and rod baffles arranged inside the first shell; and a distribution ring is arranged at the process gas inlet 18. Further, the first shell is a tube shell structure arranged vertically. Boiler water enters the U-tube bundles on the tube side from the first boiler water inlet, flows out from the boiler water outlet after being heated, and enters the super high-pressure steam drum 7. Process gas enters the distribution ring from the process gas inlet on the shell side, enters the U-tube bundle after being distributed, and then flows downwards along the U-tube bundles. Since only the rod baffles are arranged between the tube bundles, a dead zone is not present, dust in the process gas flows downwards and does not accumulate in the device. Finally, cooled process gas with dust flows out from the process gas outlet arranged at the bottom of the device and enters the switching cooler 6.

Figure 2:
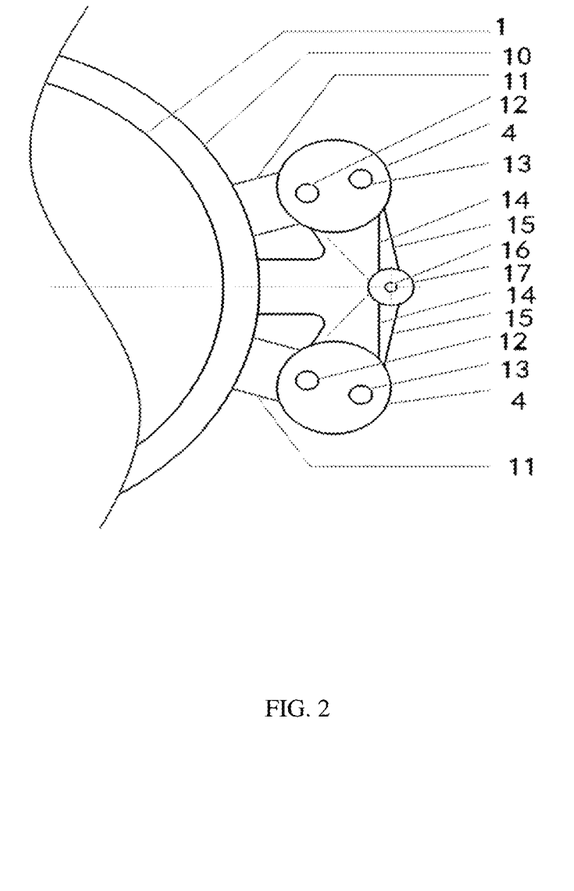
FIG. 2 is a top view of arrangement of molten salt coolers and a molten salt regulating valve of the disclosure.

Referring to FIG. 2, more than one molten salt coolers 4 are arranged and sequentially connected in series to the super high-pressure steam drum 7 respectively.

Referring to FIG. 2, the molten salt regulating valve 3 is connected to the at least two molten salt coolers 4 through cold salt channels 14 and hot salt channels 15; the molten salt coolers 4 are connected to the oxidation reactor 1 through a reactor salt channel 10; and a second boiler water inlet 12 and a steam water mixture outlet 13 are arranged on each of the molten salt coolers 4. The flow rate of hot molten salt is controlled by the core of the molten salt regulating valve 3, and hot molten salt enters the molten salt coolers 4 through the hot salt channels, flows out of the molten salt coolers 4 after being cooled, enters the cold salt channels, and returns to the reactor salt channel 10. High-pressure boiler water enters the tube side inlets of the molten salt coolers 4, and after being heated and vaporized, a steam water mixture is discharged from the tube side outlets and enters the steam drum.

Referring to FIG. 2, a support beam 11 is arranged between the molten salt coolers 4 and the oxidation reactor 1.

Further, the installation height of the super high-pressure steam drum 7 is 10-25 m higher than that of the molten salt coolers 4.

A method for producing high-pressure or super high-pressure steam as a byproduct from a maleic anhydride producing device, including the following steps:
a) heat recovery from low-temperature process gas: boiler feedwater passes through a shell pass of the switching cooler 6 and is heated by low-temperature reacted process gas in a tube pass;
b) boiler water pressure boosting: the pressure of boiler water flowing out of the switching cooler 6 is boosted by using the boiler water booster pump 9 high enough to enter the super high-pressure steam drum 7;
c) heat recovery from high-temperature process gas: the boosted boiler water is conveyed into the gas cooler 5 and heated by high-temperature process gas at the outlet of the oxidation reactor 1; and
d) generation of high-pressure or super high-pressure steam: the heated boiler water enters the super high-pressure steam drum 7 and then enters the molten salt coolers 4, and the generated high-pressure or super high-pressure steam is separated from a liquid phase in the drum 7 and flows out.

Further, in step a), the temperature of boiler feedwater entering the switching cooler 6 is less than or equal to 125° C.; the pressure of the boiler feedwater entering the switching cooler is less than or equal to 4 MPa; and the temperature of process gas entering the switching cooler is 240-300° C.

Further, the shell pass of the switching cooler 6 uses a lower pressure design, with an operating pressure of 2 MPag and a design pressure of 2.5 MPag, which further simplifies the design of expansion joints and reduces device investment.

Further, in step b), boiler water enters the boiler water buffer tank 8 or the high-pressure deaerator before being boosted by the pump; the operating pressure of the boiler water entering the boiler water buffer tank 8 is less than or equal to 3 MPag; and the operating pressure of the boiler water entering the high-pressure deaerator is 0.3-2.0 MPag.

Further, the boiler water booster pump 9 uses a centrifugal pump, and a driving machine of the centrifugal pump may be an electric motor or a steam turbine.

Further, in step c), the boosted boiler feedwater enters the tube pass of the gas cooler 5.

Further, in step c), the temperature of the heated boiler water is greater than or equal to 240° C.

Further, in step c), the temperature of the heated boiler water is greater than or equal to 280° C.

Further, in step d), the operating pressure of the drum is less than or equal to 15.6 MPag.

Further, in step d), the operating pressure of the drum is greater than or equal to 5.5 MPag.

Further, in step d), the operating pressure of the drum is greater than or equal to 7.0 MPag.

Example 1

Taking a reaction unit of a single production line with a scale of 67,000 tons/year of maleic anhydride as an example.

One tubular fixed-bed reactor was used. The feed rate of n-butane (98 mol % in purity) was 8,840 kg/h. The concentration of the n-butane in gas S1 entering the oxidation reactor 1 was 1.85 mol %. The reaction temperature was 420° C., the conversion rate of the n-butane was 85%, and the weight yield of maleic anhydride at the reactor outlet was 98 wt % (8.55 t/h). Heat released was conducted out by the shell side molten salt and conveyed to the molten salt coolers to produce 15.6 MPag of steam. Two molten salt coolers are arranged. The temperature of process gas S2 after the reaction was 420° C. In addition to the ~1 mol % reaction product maleic anhydride, the gas also contained $O_2$, $N_2$, CO, $CO_2$, $H_2O$ and other components, as well as dust blown off a catalyst bed and high freezing point tar generated during the reaction. Heat was exchanged between the reacted process gas and boiler feedwater to recover the heat.

Boiler feedwater S5 entering the switching cooler 6 was pretreated, and the oxygen content in the boiler feedwater was required to be less than or equal to 7 μg/L, which could be achieved by a high-pressure or medium-pressure thermal deaerator. In addition, hydrogen conductivity (25° C.), hardness, iron, copper, sodium, silica, chloride ions, TOCi and other indicators also had to meet the requirements of GBT 12145-2016. Since the temperature of the boiler feedwater flowing out of the deaerator was high, which was generally 133-158° C., the boiler feedwater could not cool the reaction process gas to 130° C. In addition, due to changes in the initial and final operating conditions of the switching cooler 6 (a decrease in the heat transfer effect due to tar precipitation), the temperature of the boiler feedwater needed to be adjusted to adjust the heat transfer temperature difference of the switching cooler 6 to adapt to the changes in the operating conditions throughout the entire operating cycle. Therefore, before the boiler feedwater entered the switching cooler 6, the boiler feedwater needed to be cooled to adjust the temperature. In this example, the temperature of the boiler feedwater entering the switching cooler 6 was 105° C.

(in a scaling state) and 120° C. (in a clean state), and heat generated by temperature adjustment might be used to produce low-pressure steam or hot water.

After water treatment and temperature adjustment, the low-temperature and low-pressure boiler feedwater S5 (105-120° C., 2.2 Mpag) entered the shell pass of the switching cooler 6, and cooled reacted process gas S3 from 275° C. to 130° C. (S4), while the boiler feedwater was heated to 195-209° C. (S6, corresponding to the inlet water temperature).

The heated boiler water entered the boiler water buffer tank, and the operating pressure of the boiler water buffer tank was 1.5 MPag (the pressure takes into account that when the switching cooler 6 was in the final scaling state, the lower boiler water temperature could still maintain the operating pressure when entering the boiler water buffer tank). When the switching cooler 6 was in a clean state, a small amount of higher-temperature boiler feedwater S6 was flashed when entering the boiler water buffer tank. The flashed 1.5 MPag steam entered a 1.5 MPag steam network, and the pipeline was not provided with a pressure control valve. The pressure of saturated water of 1.5 MPag and 201° C. in the boiler water buffer tank was boosted to 16.2 MPa by the boiler water booster pump, and then conveyed to the tube pass of the gas cooler 5.

High-pressure boiler feedwater S7 exchanged heat with the process gas S2 at the reactor outlet in the gas cooler 5. The reacted process gas S2 passed through the shell pass of the gas cooler 5, and cooled from 420° C. to 275° C. (S3). The high-pressure boiler feedwater S7 passed through the tube pass of the gas cooler 5, increased from 205° C. (the work of the pump caused the boiler water to rise in temperature) to 291° C. (S8) in temperature, and then entered the super high-pressure steam drum 7.

The operating pressure of the super high-pressure steam drum 7 was 15.6 MPag, and the operating temperature was 346° C. at the corresponding saturation temperature. Due to pressure rise in byproduct steam, the steam density also increased, while the density of the boiler water decreased with the increase in temperature. Therefore, the density difference between the steam and the boiler water was much smaller compared to a traditional process for producing byproduct steam of 4.0-5.5 MPag. Accordingly, the super high-pressure steam drum was typically arranged at a higher position. In this example, the super high-pressure steam drum 7 was 20 m higher than the molten salt coolers. The boiler water in the super high-pressure steam drum entered the molten salt coolers and was heated by hot molten salt of 420° C. to form a steam water mixture, and the steam water mixture was then fed into the super high-pressure steam drum 7. After steam-liquid separation, the byproduct super high-pressure steam (15.6 MPag, with a flow rate of 94.1 t/h) flowed out from the steam drum outlet. On average, for every 1 t of maleic anhydride produced, 11.0 t of byproduct super high-pressure steam of 15.6 MPag was produced.

In FIG. 3, the flow rate of hot molten salt is controlled by the core of the molten salt regulating valve, and hot molten salt enters the molten salt coolers 4 through the hot salt channels 15, flows out of the molten salt coolers 4 after being cooled, enters the cold salt channels 14, and returns to the reactor salt channel 10. High-pressure boiler water enters the tube side inlets of the molten salt coolers 4, and after being heated and vaporized, a steam water mixture is discharged from the tube side outlets and enters the steam drum.

Stream data is shown in Table 1.

TABLE 1

| Stream No. | S1 | S2 | S3 | S4 | S5 | S6 | S7 | S8 | S9 |
|---|---|---|---|---|---|---|---|---|---|
| Vapor fraction, mol | 1.0 | 1.0 | 1.0 | 1.0 | 0 | 0 | 0 | 0 | 1.0 |
| Temperature, ° C. | 165 | 420 | 275 | 130 | 105-120 | 195-209 | 205 | 291 | 346 |
| Pressure, MPag | 0.2 | 0.1 | 0.08 | 0.05 | 2.0 | 1.95 | 16.2 | 16.15 | 15.6 |
| Flow rate, kg/h | 234194 | 234194 | 234194 | 234194 | 99189 | 99189 | 99008 | 99008 | 94059 |
| Composition, mol/mol | | | | | | | | | |
| Water | 3.00% | 9.72% | 9.72% | 9.72% | 100% | 100% | 100% | 100% | 100% |
| Nitrogen | 75.14% | 73.80% | 73.80% | 73.80% | 0% | 0% | 0% | 0% | 0% |
| Oxygen | 19.97% | 13.12% | 13.12% | 13.12% | 0% | 0% | 0% | 0% | 0% |
| N-butane | 1.85% | 0.28% | 0.28% | 0.28% | 0% | 0% | 0% | 0% | 0% |
| Maleic anhydride | 0% | 1.06% | 1.06% | 1.06% | 0% | 0% | 0% | 0% | 0% |
| $CO + CO_2$ | 0% | 2.00% | 2.00% | 2.00% | 0% | 0% | 0% | 0% | 0% |

Example 2

The boiler water buffer tank was replaced with a high-pressure deaerator. The operating pressure of the high-pressure deaerator was 1.0 MPag, and hot water entering the switching cooler was boiler feedwater of 90-105° C. Other conditions were the same as in Example 1.

Stream data is shown in Table 2.

TABLE 2

| Stream No. | S1 | S2 | S3 | S4 | S5 | S6 |
|---|---|---|---|---|---|---|
| Vapor fraction, mol | 1.0 | 1.0 | 1.0 | 1.0 | 0 | 0 |
| Temperature, ° C. | 165 | 420 | 255 | 130 | 90-105 | 155-170 |
| Pressure, MPag | 0.2 | 0.1 | 0.08 | 0.05 | 1.5 | 1.45 |
| Flow rate, kg/h | 234194 | 234194 | 234194 | 234194 | 120000 | 120000 |
| Composition, mol/mol | | | | | | |
| Water | 3.00% | 9.72% | 9.72% | 9.72% | 100% | 100% |
| Nitrogen | 75.14% | 73.80% | 73.80% | 73.80% | 0% | 0% |
| Oxygen | 19.97% | 13.12% | 13.12% | 13.12% | 0% | 0% |

TABLE 2-continued

| | | | | | | |
|---|---|---|---|---|---|---|
| N-butane | 1.85% | 0.28% | 0.28% | 0.28% | 0% | 0% |
| Maleic anhydride | 0% | 1.06% | 1.06% | 1.06% | 0% | 0% |
| CO + CO$_2$ | 0% | 2.00% | 2.00% | 2.00% | 0% | 0% |

| Stream No. | S7 | S8 | S9 | S10 | S11 | S12 |
|---|---|---|---|---|---|---|
| Vapor fraction, mol | 0 | 1.0 | 0 | 0 | 0 | 1.0 |
| Temperature, °C. | 155-170 | 201 | 184 | 188 | 286 | 346 |
| Pressure, MPag | 1.45 | 1.5 | 1.0 | 16.8 | 16.75 | 15.6 |
| Flow rate, kg/h | 22272 | 5571-8857 | 97728 | 97728 | 97728 | 92835 |
| Composition, mol/mol | | | | | | |
| Water | 100% | 100% | 100% | 100% | 100% | 100% |
| Nitrogen | 0% | 0% | 0% | 0% | 0% | 0% |
| Oxygen | 0% | 0% | 0% | 0% | 0% | 0% |
| N-butane | 0% | 0% | 0% | 0% | 0% | 0% |
| Maleic anhydride | 0% | 0% | 0% | 0% | 0% | 0% |
| CO + CO$_2$ | 0% | 0% | 0% | 0% | 0% | 0% |

Adaptive changes made according to actual needs are all within the scope of protection of the disclosure.

It should be noted that for those skilled in the art, it is evident that the disclosure is not limited to the details of exemplary examples mentioned above, and can be implemented in other specific forms without departing from the spirit or basic features of the disclosure. Therefore, from any perspective, the examples should be regarded as exemplary and nonrestrictive. The scope of the disclosure is limited by the attached claims rather than the above description, and therefore aims to encompass all changes within the meaning and scope of equivalent elements of the claims. Any reference numerals in the claims should not be regarded as limiting the claims involved.

What is claimed is:

1. A device for producing high-pressure or super high-pressure steam as a byproduct from a maleic anhydride producing device, comprising a super high-pressure steam drum as well as a first path and a second path respectively connected in parallel to the super high-pressure steam drum, wherein
the first path comprises a molten salt pump, an oxidation reactor, a regulating valve and molten salt coolers sequentially connected; the second path comprises a switching cooler and a gas cooler sequentially connected; a boiler water buffer device and a boiler water booster pump are sequentially arranged and connected between the switching cooler and the gas cooler; and
the gas cooler comprises a first shell, a first boiler water inlet and a first boiler water outlet arranged at a top of the first shell, a process gas outlet arranged at a bottom of the first shell, a process gas inlet arranged at the side of the first shell, and a plurality of U-tube bundles and rod baffles arranged inside the first shell; the process gas then flows downwards along the U-tube bundles; since only the rod baffles are arranged between the tube bundles, a dead zone is not present; and a distribution ring is arranged at the process gas inlet.

2. The device for producing high-pressure or super high-pressure steam as the byproduct from the maleic anhydride producing device according to claim 1, wherein the boiler water buffer device is a boiler water buffer tank or a high-pressure deaerator.

3. The device for producing high-pressure or super high-pressure steam as the byproduct from the maleic anhydride producing device according to claim 1, wherein more than one molten salt coolers are arranged and sequentially connected in series to the super high-pressure steam drum respectively.

4. The device for producing high-pressure or super high-pressure steam as the byproduct from the maleic anhydride producing device according to claim 3, wherein the molten salt regulating valve is connected to the at least two molten salt coolers through cold salt channels and hot salt channels; the molten salt coolers are connected to the oxidation reactor through a reactor salt channel; and a second boiler water inlet and a steam water mixture outlet are arranged on each of the molten salt coolers.

5. The device for producing high-pressure or super high-pressure steam as the byproduct from the maleic anhydride producing device according to claim 4, wherein a support beam is arranged between the molten salt coolers and the oxidation reactor.

6. The device for producing high-pressure or super high-pressure steam as the byproduct from the maleic anhydride producing device according to claim 1, wherein the installation height of the super high-pressure steam drum is 10-25 m higher than that of the molten salt coolers.

7. A method for producing high-pressure or super high-pressure steam as a byproduct from a maleic anhydride producing device, comprising the following steps:
a) heat recovery from low-temperature process gas: boiler feedwater passes through a shell pass of the switching cooler and is heated by low-temperature reacted process gas in a tube pass;
b) boiler water pressure boosting: the pressure of boiler water flowing out of the switching cooler is boosted by using the boiler water booster pump high enough to enter the super high-pressure steam drum;
c) heat recovery from high-temperature process gas: the boosted boiler water is conveyed into the gas cooler and heated by high-temperature process gas at the outlet of the oxidation reactor; and
d) generation of high-pressure or super high-pressure steam: the heated boiler water enters the super high-pressure steam drum and then enters the molten salt coolers, and the generated high-pressure or super high-pressure steam is separated from a liquid phase in the drum and flows out;
wherein in step a), the temperature of boiler feedwater entering the switching cooler is less than or equal to 125° C.; the pressure of the boiler feedwater entering the switching cooler is less than or equal to 4 MPa; and the temperature of process gas entering the switching cooler is 240-300° C.;

wherein in step b), boiler water enters the boiler water buffer tank or the high-pressure deaerator before being boosted by the pump; the operating pressure of the boiler water entering the boiler water buffer tank is less than or equal to 3 MPag; and the operating pressure of the boiler water entering the high-pressure deaerator is 0.3-2.0 MPag.

* * * * *